US009468385B2

(12) United States Patent
Mazaeva et al.

(10) Patent No.: US 9,468,385 B2
(45) Date of Patent: Oct. 18, 2016

(54) VISUAL REPRESENTATION OF A CARDIAC SIGNAL SENSING TEST

(71) Applicant: Medtronic, Inc., Minneapolis, MN (US)

(72) Inventors: Natalia Y. Mazaeva, Arlington, MA (US); Janet L. Shallbetter, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/465,984

(22) Filed: Aug. 22, 2014

(65) Prior Publication Data
US 2016/0051159 A1 Feb. 25, 2016

(51) Int. Cl.
*A61B 5/04* (2006.01)
*A61B 5/0408* (2006.01)
*A61B 5/00* (2006.01)
*A61N 1/372* (2006.01)

(52) U.S. Cl.
CPC ......... *A61B 5/04011* (2013.01); *A61B 5/0031* (2013.01); *A61B 5/0408* (2013.01); *A61B 5/7221* (2013.01); *A61N 1/37247* (2013.01)

(58) Field of Classification Search
CPC .......... A61B 5/04011; A61B 5/04012; A61B 5/0452; A61B 5/04525; A61B 5/0456; A61B 5/0408; A61B 5/044; A61B 1/00045; A61B 1/00057
USPC ....................................... 600/512, 521, 523
See application file for complete search history.

(56) References Cited

U.S. PATENT DOCUMENTS

| 5,354,316 | A | 10/1994 | Keimel |
| 5,545,186 | A | 8/1996 | Olson et al. |
| 5,713,937 | A | 2/1998 | Nappholz et al. |
| 6,358,245 | B1 | 3/2002 | Edwards et al. |
| 6,418,346 | B1 | 7/2002 | Nelson et al. |
| 6,442,433 | B1 | 8/2002 | Linberg |
| 6,480,745 | B2 | 11/2002 | Nelson et al. |
| 6,522,915 | B1 | 2/2003 | Ceballos et al. |
| 6,599,250 | B2 | 7/2003 | Webb et al. |
| 6,622,048 | B1 | 9/2003 | Mann et al. |
| 6,842,644 | B2 | 1/2005 | Anderson et al. |
| 7,031,771 | B2 | 4/2006 | Brown et al. |
| 7,218,968 | B2 | 5/2007 | Condie et al. |
| 7,676,273 | B2 | 3/2010 | Goetz et al. |
| 7,904,153 | B2 | 3/2011 | Greenhut et al. |

(Continued)

FOREIGN PATENT DOCUMENTS

WO 2012019036 2/2012

OTHER PUBLICATIONS (PCT/US2015/045175) PCT Notification of Transmittal of the International Search Report and the Written Opinion of the International Searching Authority, Mailed Nov. 17, 2015, 12 pages.

*Primary Examiner* — Paula J Stice

(57) ABSTRACT

A medical device system for monitoring a patient's heart includes an implantable medical device (IMD) configured to determine sensing vector data for multiple sensing vectors selected from electrodes coupled to the IMD. The system further includes an external device configured to receive the sensing vector data and provide at least a portion of the sensing vector data to a user display configured to display sensing vector criteria and the sensing vector data as part of a graphical user interface for programming a sensing vector used by the implantable medical device for monitoring a patient's heart rhythm.

23 Claims, 6 Drawing Sheets

(56) References Cited

U.S. PATENT DOCUMENTS

| | | |
|---|---|---|
| 8,160,684 B2 | 4/2012 | Ghanem et al. |
| 8,355,784 B2 | 1/2013 | Rochat et al. |
| 8,437,842 B2 | 5/2013 | Zhang et al. |
| 8,483,829 B2 | 7/2013 | Rochat et al. |
| 2007/0239220 A1* | 10/2007 | Greenhut et al. ............ 607/32 |
| 2007/0276445 A1 | 11/2007 | Sanghera et al. |
| 2008/0172100 A1 | 7/2008 | Sanghera et al. |
| 2008/0269813 A1 | 10/2008 | Greenhut et al. |
| 2013/0197381 A1* | 8/2013 | Charlton ............ A61B 5/686 600/523 |
| 2014/0005742 A1* | 1/2014 | Mahajan et al. ............ 607/28 |
| 2015/0305638 A1* | 10/2015 | Zhang ............ A61B 5/04011 600/512 |

\* cited by examiner

VISUAL REPRESENTATION OF A CARDIAC SIGNAL SENSING TEST

TECHNICAL FIELD

The disclosure relates generally to implantable medical device systems and, in particular, to an apparatus and method for performing a cardiac signal sensing test and producing a visual representation of the test results.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. Additionally or alternatively, some IMDs may include electrodes or other sensors positioned along the housing of the IMD. IMDs may deliver therapy to or monitor conditions of a variety of organs, nerves, muscle or tissue, such as the heart, brain, stomach, spinal cord, pelvic floor, or the like. Electrodes or other sensors on the IMD housing or carried by a lead are positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), monitor the heart of the patient via sensing electrodes and deliver cardiac electrical stimulation therapies via therapy delivery electrodes. The electrodes may be carried by one or more implantable leads. The leads may be transvenous, i.e., implanted in the heart or a blood vessel through one or more veins. Other leads may be non-transvenous leads implanted outside the heart. In other cases, electrodes may be carried by a housing of the IMD. In any of these cases, the electrodes are used to sense cardiac electrical signals for detecting cardiac conditions and/or for providing electrical stimulation such as pacing pulses, cardioversion shocks or defibrillation shocks to address abnormal cardiac rhythms (such as bradycardia, tachycardia or fibrillation), heart failure or other cardiac conditions.

The IMD senses signals representative of intrinsic depolarizations of the heart and analyzes the sensed signals to identify normal or abnormal rhythms. Upon detection of an abnormal rhythm, the device may deliver an appropriate electrical stimulation signal or signals to restore or maintain a more normal rhythm. For example, an IMD may deliver pacing pulses to the heart upon detecting tachycardia or bradycardia, and deliver cardioversion or defibrillation shocks to the heart upon detecting tachycardia or fibrillation.

In general, a clinician selects values for a number of programmable parameters that control the sensing functions of the IMD and the cardiac electrical stimulation therapy to be delivered by the IMD. Numerous programmable parameters may be available for controlling both the sensing and therapy delivery functions. The programmer may be used to interrogate the IMD to retrieve values of control parameters that have been programmed into the IMD. The programmable parameters may be accessed by the clinician or another user interacting with a programmer that wirelessly transmits programming data to the IMD. The clinician may select parameters to be programmed and select a setting or value of the programmable parameter using the programmer.

SUMMARY

In general, the disclosure is directed to techniques for visually representing results of sensing tests performed by an IMD. An IMD system operating in accordance with the techniques performs a sensing test to evaluate multiple sensing vectors selected from available electrodes. Sensing vector data is collected by the IMD and transmitted to an external device. The system produces a visual display of sensing vector data on a user display of the external device as part of a graphical user interface to facilitate selection and programming of sensing vectors used by the IMD to monitor the heart rhythm.

In one example, the disclosure provides a method including sensing cardiac electrical signals across a plurality of sensing vectors selected from a plurality of implantable electrodes coupled to an implantable medical device, determining sensing vector data from the sensed cardiac electrical signals for each of the plurality of sensing vectors, wirelessly transmitting the sensing vector data by an implantable telemetry module, receiving the transmitted sensing vector data by an external telemetry module of an external medical device, providing, by an external processor coupled to the external telemetry module, sensing vector acceptability criteria and at least a portion of the sensing vector data to a user display, and displaying the sensing vector acceptability criteria and at least the portion of the sensing vector data as part of a graphical user interface for programming a sensing vector used by the implantable medical device for monitoring a patient's heart rhythm.

In another example, medical device system includes a plurality of implantable electrodes, an implantable medical device, an external telemetry module, a user display and an external processor. The implantable medical device includes a sensing module configured to sense cardiac electrical signals across a plurality of sensing vectors selected from the plurality of electrodes, a processor coupled to the sensing module and configured to determine sensing vector data for each of the plurality of sensing vectors from the sensed cardiac electrical signals, and a telemetry module configured to transmit the sensing vector data. The external telemetry module is configured to receive the transmitted sensing vector data. The external processor is coupled to the user display and the external telemetry module and is configured to provide sensing vector acceptability criteria and at least a portion of the sensing vector data to the user display. The user display is configured to display the sensing vector criteria and the sensing vector data received from the external processor as part of a graphical user interface for programming a sensing vector used by the implantable medical device for monitoring a patient's heart rhythm.

In yet another example, a non-transitory, computer-readable medium stores a set of instructions, which when executed by a processor of a medical device system causes the system to sense cardiac electrical signals across a plurality of sensing vectors selected from a plurality of implantable electrodes coupled to an implantable medical device, determine sensing vector data from the sensed cardiac electrical signals for each of the plurality of sensing vectors, wirelessly transmit the sensing vector data by an implantable telemetry module, receive the transmitted sensing vector data by an external telemetry module of an external medical device, provide, by an external processor coupled to the external telemetry module, sensing vector acceptability criteria and at least a portion of the sensing vector data to a user display; and display the sensing vector acceptability criteria and at least the portion of the sensing vector data as part of a graphical user interface for programming a sensing vector used by the implantable medical device for monitoring a patient's heart rhythm.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

An implantable medical device system, according to the present disclosure determines cardiac signal sensing vector data and produces a display of at least a portion of the sensing vector data together with a sensing vector acceptability criteria as part of a graphical user interface. The graphical user interface promotes understanding of the sensing vector data and acceptability criteria by a clinician or other user and facilitates selection and programming of sensing vectors used by an IMD for monitoring cardiac electrical signals for detecting and discriminating heart rhythms.

Figure 1:
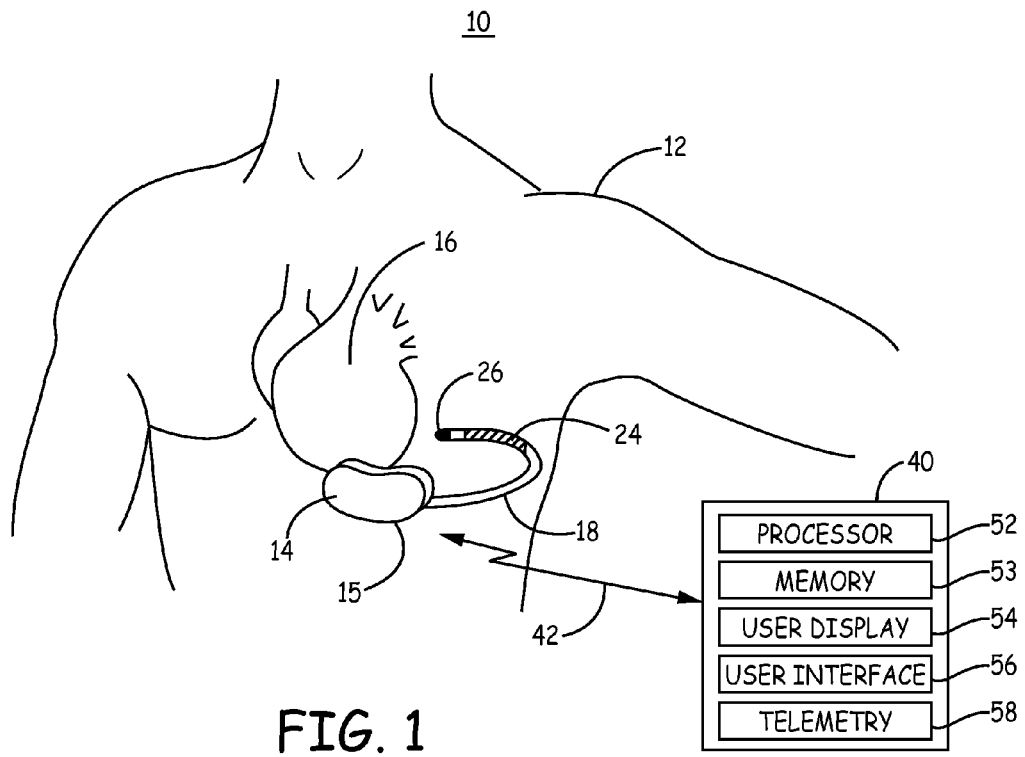
FIG. 1 and FIG. 2 are conceptual diagrams of an IMD system, shown implanted in a patient, in which techniques described herein may be usefully practiced.
Figure 2:
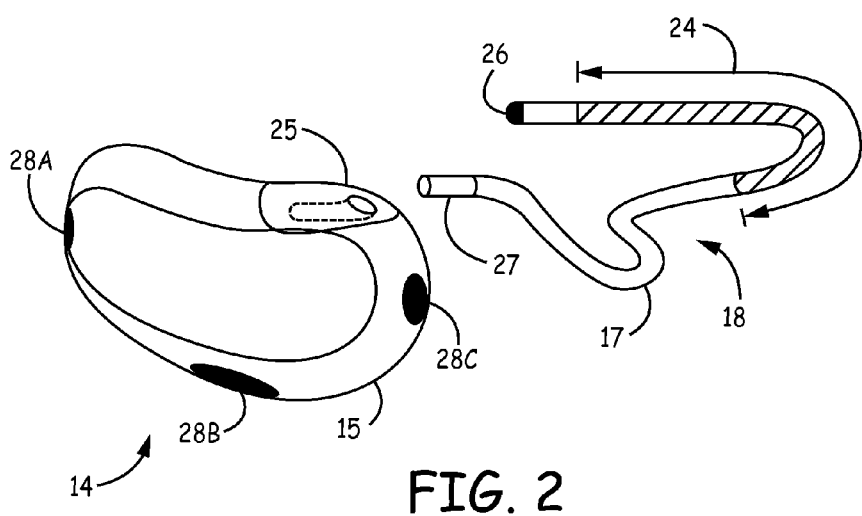

FIG. 1 and FIG. 2 are conceptual diagrams of an IMD system 10, shown implanted in a patient 12, in which techniques described herein may be usefully practiced. As illustrated in FIG. 1, IMD system 10 includes an IMD 14 and an external device 40. IMD 14 may be implanted subcutaneously or submuscularly outside the ribcage of a patient 12, e.g., anterior to the cardiac notch. IMD 14 includes a housing 15 to enclose electronic circuitry of the IMD 14.

A sensing and cardioversion/defibrillation therapy delivery lead 18 is electrically coupled to IMD 14 is tunneled subcutaneously into a posterior location, e.g., adjacent to a portion of a latissimus dorsi muscle of patient 12. Lead 18 may be tunneled subcutaneously from a medial implant pocket of IMD 14 laterally and posteriorly to the patient's back to a location generally opposite the heart 16 such that the heart 16 is disposed between IMD 14 and a distal defibrillation electrode 24 and a distal sensing electrode 26 of lead 18.

Subcutaneous lead 18 includes a distal defibrillation coil electrode 24, which may be a coil electrode or other relatively large surface area electrode, for delivering high voltage cardioversion or defibrillation shocks to heart 16 for terminating a malignant tachyarrhythmia. Subcutaneous lead 18 may further include a distal sensing electrode 26, used for sensing cardiac electrical signals, e.g., subcutaneous electrocardiogram (ECG) signals, for monitoring heart 16. Distal sensing electrode 26 may be a ring, tip electrode or other relatively lower surface area electrode than defibrillation electrode 24.

The electrodes 24 and 26 are carried by an elongated, insulated flexible lead body 17 (shown in FIG. 2). Lead body 17 may be formed from a non-conductive material, such as silicone, polyurethane, fluoropolymers, or mixtures thereof or other appropriate materials, and is shaped to form one or more lumens within which the one or more electrical conductors extend. The electrical conductors (not illustrated) extend from each of the respective distal electrodes 24 and 26 to a proximal connector pin 27. Connector pin 27 is adapted for connection to IMD 14 via a connector assembly 25, also sometimes referred to as a "connector block" or "header. Connector assembly 25 includes a connector bore for receiving connector pin 27 and the necessary electrical connectors and feedthroughs crossing IMD housing 15 for electrically coupling electrodes 24 and 26 to IMD circuitry enclosed within housing 15. The electrical conductors transmit therapy from a therapy module within IMD 14 to electrode 24 and transmit sensed electrical signals from sensing electrode 26 to a sensing module within IMD 14. While lead 18 is shown carrying a single sensing electrode 26, lead 18 may be configured with two or more sensing electrodes in other examples for providing cardiac electrical signals to a sensing module within IMD 14. Sensing electrodes may be carried along any portion of lead body 17, i.e., more proximal than defibrillation electrode 24 and/or distal to defibrillation electrode 24.

In addition, one or more electrodes may be positioned along the outer surface of IMD housing 15. In the example shown, three housing-based electrodes 28A, 28B, 28C, also referred to collectively as electrodes 28, are provided along housing 15. Housing-based electrodes may be positioned along the housing 15 using a surround shroud as generally disclosed in U.S. Pat. No. 6,522,915 (Ceballos, et al.), incorporated herein by reference in its entirety. In other examples all or a portion of housing 15 may define a housing electrode, sometimes referred to as a "CAN electrode," that can be used in combination with a distal electrode 24 or 26 for delivering a cardiac therapy or sensing ECG signals. When housing 15 serves as an electrode and housing-based electrodes 28 are present, housing 15 is electrically isolated from electrodes 28. As will be described in further detail herein, housing 15 may enclose one or more processors, memory devices, transmitters, receivers, sensors, sensing circuitry, therapy circuitry and other appropriate components.

Electrodes 28 and distal sensing electrode 26 may be selected in any combination for sensing cardiac electrical signals. Three housing-based sensing vectors are available using each combination of electrodes 28A and 28B, electrodes 28A and 28C and electrodes 28B and 28C. Electrodes 28 may be selected individually or in any combination with distal sensing electrode 26. In one example, at least four different sensing vectors are tested for sensing vector signal quality using the three housing-based electrode combinations and one combination of a housing-based electrode 28A, 28B or 28C and distal sensing electrode 26. In other examples, additional vectors using each one of the housing-based electrodes 28 may be tested in combination with the distal sensing electrode 26 for a total of six sensing vectors (three housing-based sensing vectors and three vectors employing distal sensing electrode 26 and one housing based electrode 28A, 28B and 28C one at a time. In still other examples, additional sensing vectors tested for sensing vector signal quality may employ defibrillation electrode 24. IMD 14 acquires sensing vector data during a sensing test to provide the sensing vector data to an external device 40 for visual representation to a user.

The lead and electrode configuration shown in FIG. 1 is illustrative of one arrangement of electrodes that can be used for sensing subcutaneous ECG signals and delivering cardioversion/defibrillation shocks. In other examples, one or more housing-based electrodes and/or one or more lead-based electrodes carried by one or more leads extending away from IMD 14 may be provided and available for use in various combinations to provide multiple, selectable ECG sensing vectors. Such configurations enable sensing of ECG signals using non-transvenous extra-cardiac electrodes implanted beneath the skin, muscle or other tissue layer within a patient's body.

Further referring to FIG. 1, an external device 40 is shown in telemetric communication with IMD 14 by an RF communication link 42. External device 40 is often referred to as a "programmer" because it is typically used by a physician, technician, nurse, clinician or other qualified user for programming operating parameters in IMD 14. External device 40 may be located in a clinic, hospital or other medical facility. External device 40 may alternatively be embodied as a home monitor or a handheld device that may be used in a medical facility, in the patient's home, or another location. Operating parameters, such as sensing and therapy delivery control parameters, may be programmed into IMD 14 using external device 40.

External device 40 includes a processor 52 and associated memory 53, user display 54, user interface 56 and telemetry module 58. Processor 52 controls external device operations and processes data and signals received from IMD 14. According to techniques disclosed herein, processor 52 receives sensing vector data obtained by IMD 14 and transmitted to telemetry module 58 from IMD 14. Processor 52 provides user display 54 with at least a portion of the sensing vector data along with sensing vector acceptability criteria that may be stored in memory 53 for display to a user.

Processor 52 may analyze the sensing vector data received from IMD 14 prior to providing the data to user display 54. In some examples, processor 52 receives sensing vector data as raw cardiac electrical signals. Processor 52 may be configured to determine sensing vector selection parameters from the sensing vector data and provide the sensing vector selection parameters determined for each sensing vector tested by the IMD 14 to user display 54. In other examples, IMD 14 determines the sensing vector selection parameters from cardiac electrical signals during a test performed by IMD 14. The sensing vector data transmitted to external device 40 from IMD 14 includes the sensing vector selection parameters. The processor 52 receives the sensing vector data and provides at least the sensing vector selection parameters to user display 54. A processor configured to determine sensing vector selection parameters from cardiac electrical signals received by IMD 14 may be an implantable processor included in IMD 14, the external processor 52 included in external device 40 or a combination of both.

The user display 54 provides a display of the sensing vector data and sensing vector acceptability criteria received from processor 52. The display may be a part of a graphical user interface that facilitates programming of one or more sensing vectors by a user interacting with external device 40. External device 40 may display other data and information relating to IMD functions to a user for reviewing IMD operation and programmed parameters as well as ECG signals or other physiological data that is retrieved from IMD 14 during an interrogation session. User interface 56 may include a mouse, touch screen, keyboard and/or keypad to enable a user to interact with external device 40 to initiate a telemetry session with IMD 14 for retrieving data from and/or transmitting data to IMD 14 for selecting and programming desired sensing and therapy delivery control parameters into IMD 14.

Telemetry module 58 is configured for bidirectional communication with an implantable telemetry module included in IMD 14. Telemetry module 58 is configured to operate in conjunction with processor 52 for sending and receiving data relating to IMD functions via communication link 42. Communication link 42 may be established between IMD 14 and external device 40 using a radio frequency (RF) link such as BLUETOOTH®, Wi-Fi, Medical Implant Communication Service (MICS) or other RF bandwidth. In some examples, external device 40 may include a programming head that is placed proximate IMD 14 to establish and maintain a communication link, and in other examples external device 40 and IMD 14 may be configured to communicate using a distance telemetry algorithm and circuitry that does not require the use of a programming head and does not require user intervention to maintain a communication link.

It is contemplated that external device 40 may be in wired or wireless connection to a communications network via telemetry module 58 for transferring data to a remote database or computer to allow remote management of the patient 12. Remote patient management systems may be configured to utilize the presently disclosed techniques to enable a clinician to review sensing vector data and authorize programming of automatically recommended sensing vectors or manually selecting sensing vectors to be programmed in IMD 14 after viewing a visual representation of sensing vector data. For example, sensing vector data may be transferred from IMD 14 to external device 40 and from external device 40 to a computer or database that is remote from the patient for viewing at a clinic or other expert center. The clinician or other user may then authorize programming of sensing vectors and other control parameters of the IMD 14 used for sensing cardiac signals and delivering therapy via the communications network and external device 40. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of remote patient management systems that enable remote patient monitoring and device programming. Each of these patents is incorporated herein by reference in their entirety.

Figure 3:
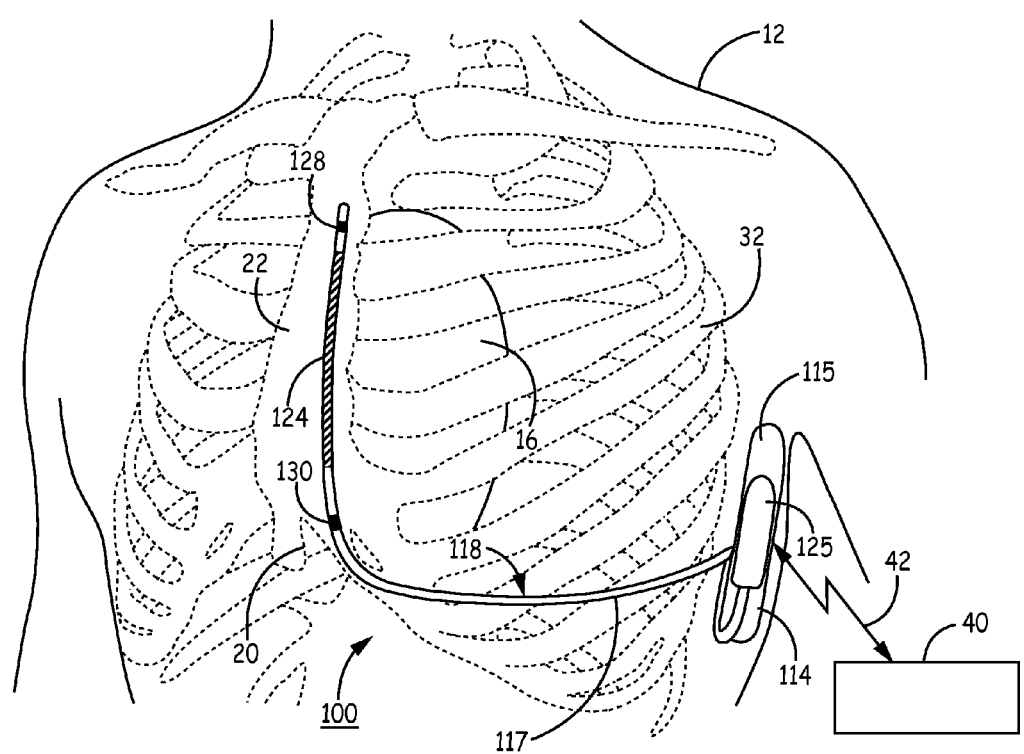
FIG. 3 is a conceptual diagram of another example of IMD system in which the techniques disclosed herein may be implemented.

FIG. 3 is a conceptual diagram of another example IMD system 100 that includes an IMD 114 coupled to a defibrillation lead 118. IMD 114 is configured for bidirectional communication with external device 40 via communication link 42 as described above. Defibrillation lead 118 includes a proximal end that is connected to IMD 114 and a distal end that includes one or more electrodes. Defibrillation lead 118 is illustrated in FIG. 3 as being implanted subcutaneously, e.g., in tissue and/or muscle between the skin and the ribcage 32 and/or sternum 22. Defibrillation lead 118 extends subcutaneously from IMD 114 toward xiphoid process 20. At a location near xiphoid process 20 defibrillation lead 118 bends or turns and extends subcutaneously superior, substantially parallel to sternum 22. Although illustrated as being offset laterally from and extending substantially parallel to sternum 22 in the example of FIG. 3, defibrillation lead 118 may be implanted over sternum 22, offset from sternum 22, but not parallel to sternum 22 (e.g., angled laterally from sternum 22 at either the proximal or distal end of lead 118).

In other instances, lead 118 may be implanted at other extravascular locations. For example, lead 118 may be implanted at least partially in a substernal location, e.g., between the ribcage 32 and/or sternum 22 and heart 26. In one such configuration, a proximal portion of lead 118 extends subcutaneously from IMD 114 toward sternum 22 and a distal portion of lead 118 extends superior under or below the sternum 22 in the anterior mediastinum, which is bounded laterally by pleurae, posteriorly by the pericardium, and anteriorly by sternum 22. In one example, the distal portion of lead 118 extends along the posterior side of sternum 22 substantially within the loose connective tissue and/or substernal musculature of the anterior mediastinum. Lead 118 may be at least partially implanted in other intrathoracic locations, e.g., other extra-vascular, extra-pericardial locations, including the gap, tissue, or other anatomical features around the perimeter of and adjacent to, but not attached to, the pericardium or other portion of heart 16 and not above sternum 22 or ribcage 32.

In another example, IMD 114 may be implanted in a subcutaneous pocket in the right chest. In this example, defibrillation lead 118 may extend subcutaneously from the device toward the manubrium of the sternum 22 and bend or turn and extend subcutaneously or substernally inferiorly from the manubrium of the sternum 22, substantially parallel with the sternum 22.

Defibrillation lead 118 includes an elongated lead body 117 carrying electrodes 124, 128 and 130 located along the distal portion of the length of lead body 117. Lead body 117 insulates one or more elongated electrical conductors (not illustrated) that extend from a respective electrode 124, 128 and 130 through the lead body to a proximal connector (not shown) that is coupled to IMD 114. The conductors are electrically coupled to IMD circuitry, such as a therapy module or a sensing module, via connections in an IMD connector assembly 125 that includes a connector bore for receiving the proximal connector of lead 118

Defibrillation lead 118 is shown in FIG. 3 to include a defibrillation electrode 124, which may be an elongated coil electrode, along the distal portion of defibrillation lead 118. Defibrillation electrode 124 is located on lead 118 such that when IMD 114 is implanted a therapy vector between defibrillation electrode 124 and a housing or can electrode 115 of IMD 114 is substantially through or across the ventricle(s) of heart 26.

Defibrillation lead 118 also includes one or more sensing electrodes 128 and 130, which may be located toward the distal portion of defibrillation lead 116. In the example illustrated in FIG. 3, sensing electrodes 128 and 130 are separated from one another by defibrillation electrode 124. In other words, sensing electrode 128 is located distal to defibrillation electrode 124, and sensing electrode 130 is proximal to defibrillation electrode 124. IMD system 100 may sense electrical activity of heart 26 via one or more of sensing vectors that include combinations of electrodes 128 and 130 and the housing or can electrode 115 of IMD 114. For example, IMD 114 may receive an ECG signal across a sensing vector between electrodes 128 and 130, a sensing vector between electrode 128 and the conductive housing or can electrode 115, a sensing vector between electrode 130 and the conductive housing or can electrode 115, or any combination of electrodes 128, 130 and the housing or can electrode 115. In some instances, IMD 114 may even sense cardiac electrical signals using a sensing vector that includes defibrillation electrode 124.

IMD 114 receives cardiac electrical signals from one or more of the sensing vectors described above for detecting tachyarrhythmia. IMD 114 may deliver one or more cardioversion or defibrillation shocks via defibrillation electrode 124 in response to detecting ventricular tachycardia (VT) or ventricular fibrillation (VF). IMD 114 may also provide pacing therapy, such as post-shock pacing therapy, after a cardioversion or defibrillation shock using any of electrodes 124, 128, 130 and housing electrode 115.

IMD 114 includes a housing 115, also referred to herein as housing electrode or can electrode 115, which forms a hermetic seal that protects internal electronic components of IMD 114. The housing 115 may be formed of a conductive material, such as titanium, titanium alloy, or other conductive material, to serve as an electrode. Housing 115 may function as a "can electrode" since the conductive housing or a portion thereof may be coupled to internal circuitry to be used as an indifferent or ground electrode during sensing or defibrillation shock delivery. IMD 114 also includes connector assembly 125 that includes electrical feedthroughs through which electrical connections are made between electrical conductors within lead 118 and electronic components included within the housing 115.

The techniques disclosed herein may be implemented in numerous IMD and electrode configurations that include one or more housing-based electrodes and/or one or more lead-based electrodes for enabling sensing of cardiac electrical signals across multiple selectable sensing vectors. The IMD systems 10 and 100 are referred to as extravascular IMD systems because leads 18 and 118 are non-transvenous leads positioned in extravascular locations, i.e. outside the blood vessels and heart 16 of patient 12.

It is understood that while IMD 14 and 114 and associated lead 18 and 118, respectively, may be positioned between the skin and a muscle layer of the patient 12, IMDs 14 and 114 may be configured to be coupled to an epicardial lead or a transvenous lead such as an endocardial lead or coronary sinus lead in other examples. For example, an IMD system may include an IMD configured to deliver cardiac pacing and/or cardioversion/defibrillation therapies using one or more leads used to position electrodes in or along the right atrium, left atrium, right ventricle, and/or left ventricle. Examples of transvenous leads and an IMD that may be included in an IMD system operating according to the techniques disclosed herein are generally disclosed in commonly-assigned U.S. Pat. No. 8,355,784 (Rochat, et al.), incorporated herein by reference in its entirety.

Sensing vectors employed by IMD system 10 and IMD system 110 are used to receive ECG signals across the electrodes selected in a given sensing vector. When transvenous or epicardial electrodes are used, the cardiac electrical signals that are sensed are referred to as cardiac electrogram (EGM) signals. It is to be understood that the techniques disclosed herein may be used in conjunction with any cardiac electrical signals, including ECG and EGM signals and even cutaneous or external ECG signals obtained using external skin or surface electrodes.

Figure 4:
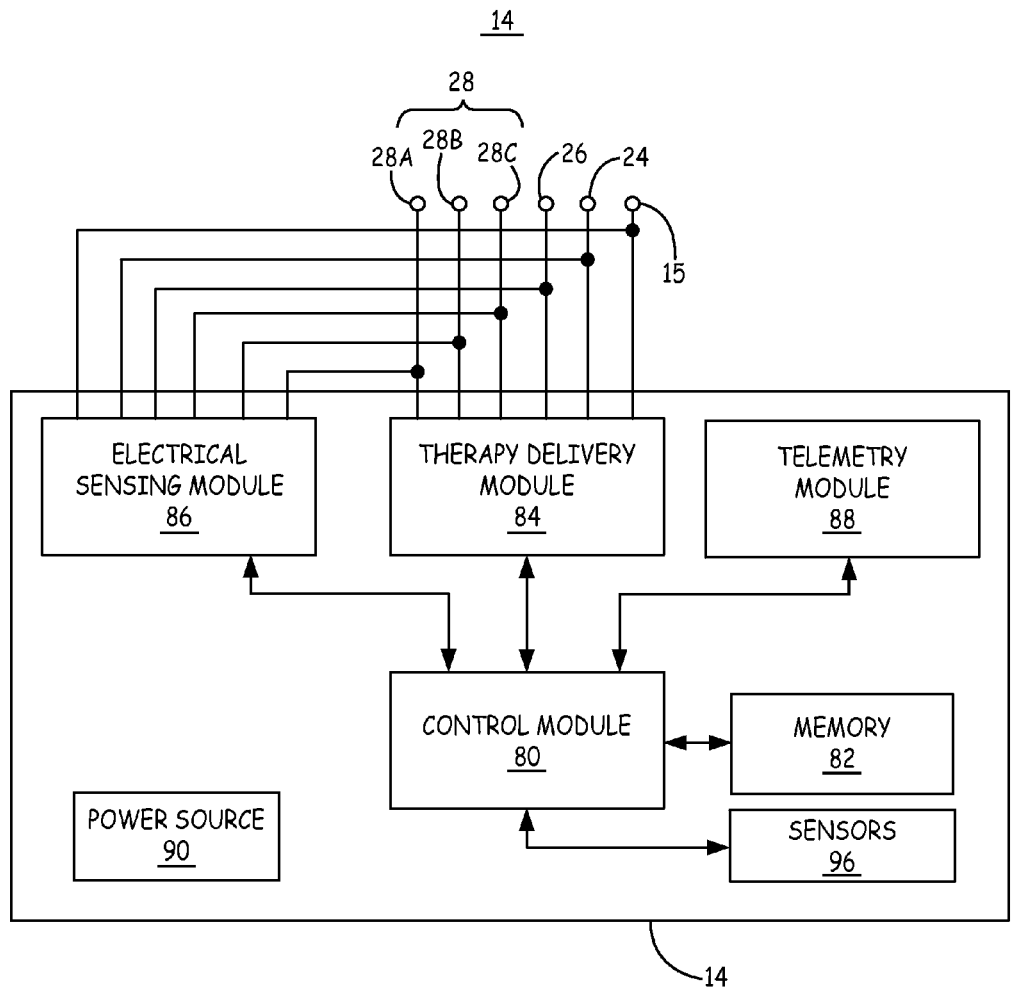
FIG. 4 is a schematic diagram of an IMD according to one embodiment.

FIG. 4 is a schematic diagram of IMD 14 according to one embodiment. The following description of circuitry that is included in IMD 14 pertains to IMD 114 shown in FIG. 3 as well. The electronic circuitry enclosed within housing 15 includes software, firmware and hardware that cooperatively monitor one or more ECG signals, determine when a cardioversion-defibrillation shock is necessary, and deliver prescribed cardioversion-defibrillation therapies. In some examples, IMD 14 is coupled to a lead, such as lead 16, carrying electrodes, such as electrodes 24 and 26, positioned in operative relation to the patient's heart 16 for delivering cardiac pacing pulses and may therefore include the capability to deliver low voltage pacing pulses as well as the high voltage cardioversion-defibrillation shock pulses.

IMD 14 includes control module 80, associated memory 82, therapy delivery module 84, electrical sensing module 86, and telemetry module 88. A power source 90 provides power to the circuitry of IMD 14, including each of the modules 80, 82, 84, 86 and 88 as needed. Power source 90 may include one or more energy storage devices, such as one or more rechargeable or non-rechargeable batteries. Connections between power source 90 and the various IMD modules 80, 82, 84, 86 and 88 are not shown in FIG. 4 for the sake of clarity.

Modules shown in FIG. 4 represent functionality that may be included in IMD 14 and may include any discrete and/or integrated electronic circuit components that implement analog and/or digital circuits capable of producing the functions attributed to IMD 14 herein. For example, the modules may include analog circuits, e.g., amplification circuits, filtering circuits, and/or other signal conditioning circuits. The modules may also include digital converters, combinational or sequential logic circuits, integrated circuits, processors (shared, dedicated, or group) and memory that execute one or more software or firmware programs, application specific integrated circuit (ASIC), memory devices, state machine, etc. As used herein, the term "module" refers to any electronic circuit or suitable components that provide the described functionality.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other IMD modules to perform various functions attributed to IMD 14. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components.

Control module 80 communicates with therapy delivery module 84 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 26, 28, and housing electrode 15, which may serve as a common or ground electrode.

Electrical sensing module 86 is selectively coupled to electrodes 24 and 28, and in some examples housing electrode 15 and defibrillation electrode 26, in order to monitor electrical activity of the patient's heart. Sensing module 86 is enabled to selectively monitor one or more sensing vectors selected from the available electrodes 24, 26, 28 and 15. For example, sensing module 86 may include switching circuitry for selecting which of electrodes 24, 26, 28 and housing electrode 15 are coupled to sense amplifiers or other sensing circuitry included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors simultaneously selected from electrodes 24, 26, 28, and housing electrode 15. For example, a sensing vector between one of electrodes 28A, 28B, and 28C and electrode 26 may be selected for sensing a first sensing vector on one channel and at least one additional sensing vector may be selected between one of the other of electrodes 28A, 28B and 28C paired with electrode 26 and received on another sensing channel. Each sensing channel may be configured to amplify and filter the ECG to improve the signal quality for sensing cardiac events, e.g., R-waves.

Each sensing channel of sensing module 86 may include a sense amplifier for receiving the ECG signals developed across the selected electrodes. The sense channels pass sense event signals to control module 80. For example R-wave sense signals may be passed to control module 80 when a received ECG signal crosses an R-wave sensing threshold, which may be an auto-adjusting sensing threshold in some instances.

Sensing module 86 may include an analog-to-digital converter for providing a digital ECG signal to control module 80 from each sensing channel. In one example, two sensing channels are provided for receiving an ECG from a first sensing vector between any two of electrodes 28A, 28B, and 28C and electrode 26 and a second sensing vector selected from a different pair of electrodes 28A, 28B and 28C and electrode 26. The two ECG signals are converted to a multi-bit digital signal by sensing module 86 and provided to control module 80 for obtaining sensing vector data.

Control module 80 includes a tachyarrhythmia detector for detecting and discriminating supraventricular tachycardia (SVT), VT and VF. Control module 80 may further include timing circuitry including various timers and/or counters for measuring time intervals, such as RR intervals, and setting time windows such as signal analysis windows. The timing of R-wave sense signals received from sensing module 86 may be used for cardiac signal analysis windows used to obtain sensing vector data.

The timing of R-wave sense signals may be used by control module 80 to measure RR intervals for monitoring the patient's heart rhythm. The control module tachyarrhythmia detector may count RR intervals measured by the timing circuit that fall into different rate detection zones for determining a ventricular rate or preforming other rate- or interval-based assessments for detecting ventricular tachyarrhythmia. Examples of algorithms that may be performed by IMD 14 for detecting, discriminating and treating tachyarrhythmia are generally disclosed in U.S. Pat. No. 5,354,316 (Keimel); U.S. Pat. No. 5,545,186 (Olson, et al.); U.S. Pat.

No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

Therapy delivery module 84 may include a high voltage (HV) therapy delivery module including one or more HV output capacitors and, in some instances, a low voltage therapy delivery module. When a malignant tachycardia is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using defibrillation electrode 24 and housing electrode 15. The control module 80 may control therapy delivery module 84 to deliver R-wave synchronized shock pulses.

It should be noted that implemented cardiac monitoring algorithms may utilize not only cardiac electrical signal analysis methods but may also utilize supplemental sensors 96, such as blood pressure, tissue oxygenation, respiration, patient activity, heart sounds, and the like, for contributing to a decision by control module 80 to apply or withhold a therapy or generally acquiring physiological signals for monitoring patient 12.

IMD telemetry module 88 includes a transceiver and antenna for communicating with external device 40 (shown in FIG. 1) using RF communication. Under the control of control module 80, telemetry module 88 may receive downlink telemetry from and send uplink telemetry to external device 40. ECG episode data related to the detection of VT or VF and the delivery of a cardioversion or defibrillation shock may be stored in memory 82. Stored episode data is transmitted by telemetry module 88 to an external device 40 upon receipt of an interrogation command. Clinician review of episode data facilitates diagnosis and prognosis of the patient's cardiac state and therapy management decisions, including selecting programmable VT/VF detection and therapy delivery control parameters.

During a sensing vector test, control module 80 controls sensing module 86 to sense an ECG signal using multiple test sensing vectors available from electrodes 24, 26, 28 and 15. Control module 80 analyzes the received ECG signals to determine sensing vector data that is stored in memory 82 and transmitted by implantable telemetry module 88 to external device 40. As described below, sensing vector selection parameters may be determined from each sensing vector signal that are used for selecting one or more sensing vectors expected to provide the most reliable sensing of cardiac electrical signals by IMD 14 for detecting and discriminating heart rhythms. In some examples, episodes of ECG signals sensed by each of the test sensing vectors may also be stored in memory 82 and transmitted to external device 40.

Figure 5:
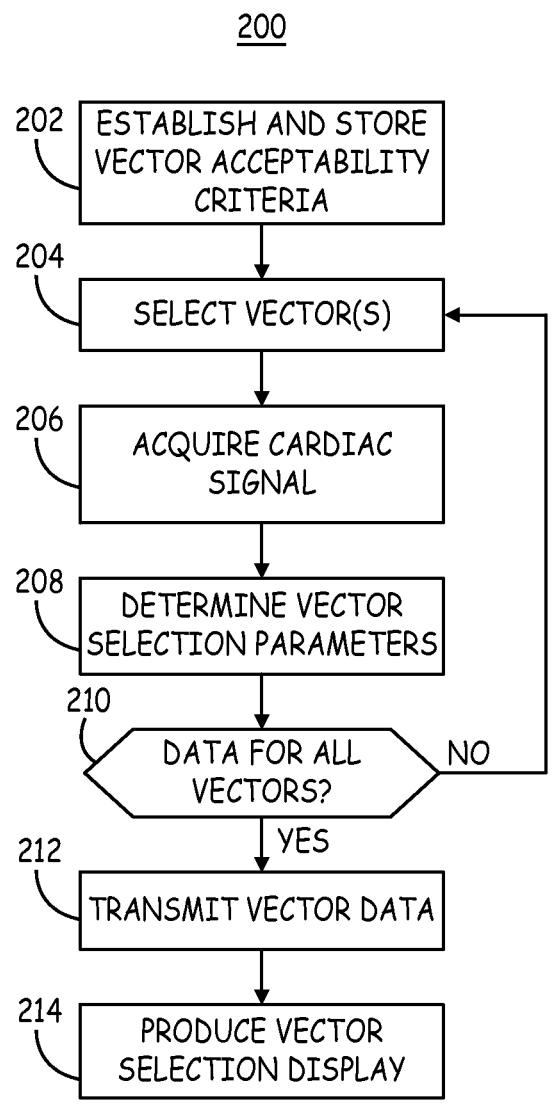
FIG. 5 is a flow chart of a method for providing vector acceptability criteria and sensing vector data as part of a graphical user interface to facilitate programming of one or more sensing vectors according to one example.

FIG. 5 is a flow chart 200 of a method for obtaining and presenting vector acceptability criteria and sensing vector data as part of a graphical user interface to facilitate selection and programming of one or more sensing vectors according to one example. At block 202, sensing vector acceptability criteria are established. Sensing vector acceptability criteria may include one or more thresholds for each of at least one sensing vector selection parameter that is determined from a cardiac electrical signal. The sensing vector acceptability criteria may include a threshold or range applied to a selection parameter. In one example, the acceptability criteria include an R-wave amplitude threshold and a low slope content threshold as further described below. The acceptability criteria may be defined as a range of each sensing vector selection parameter, e.g., an R-wave amplitude range and a low slope content range. The range may include a lower boundary of the range that represents an acceptability threshold and an upper boundary that represents a maximum possible value of the respective selection parameter.

The vector acceptability criteria may be fixed values programmed in the external device 40 and stored in memory 53. Alternatively, the vector acceptability criteria may be programmed in the IMD 14 and stored in IMD memory 82. In this case, the acceptability criteria may be programmed to patient-specific values. Vector acceptability criteria are used to discriminate between acceptable sensing vectors and unacceptable sensing vectors. In addition to vector acceptability criteria, vector selection criteria may be defined. Vector selection criteria are used to select one or more sensing vectors from the vectors that meet the vector acceptability criteria. As described below, selected sensing vectors may be programmed into the IMD for sensing cardiac signals.

At block 204, one or more vectors are initially selected to begin a sensing vector test. The sensing vector test may be initiated by a user interacting with external device 40. The user may select a "start sensing vector test" button on the user display 54 of external device 40 to initiate a sensing vector test. The sensing vector test may then be executed automatically by IMD 14 in response to a "start test" command received from external device 40. In other examples, a sensing vector test may be performed automatically by IMD 14 on a regular periodic basis, e.g., daily, weekly, monthly or other frequency. Data acquired during the test may be transmitted to external device 40 the next time a telemetry communication session is established with the IMD 14. A sensing vector test may additionally or alternatively be initiated automatically by the IMD 14 in response to suspected oversensing or undersensing of cardiac events.

When the test is initiated, a sensing vector is selected at block 204 by coupling a combination of available electrodes to the IMD sensing module 86. When multiple sensing channels are available, multiple sensing vectors can be selected to obtain sensing vector data from multiple vectors simultaneously. With reference to the example of FIGS. 1 and 2, each of the possible combinations of the housing-based electrodes 28A, 28B, 28C and lead based electrode 26 may be selected two at a time when IMD sensing module 86 includes two sensing channels. To illustrate, electrodes 28A and 28B may be selected as a first sensing vector to be tested and coupled to a first sensing channel of sensing module 86. Electrodes 28B and 28C may be selected as a second sensing vector to be tested and coupled to a second sensing channel. Sensing vector data is simultaneously obtained from both the first and second sensing vectors. Next electrodes 28A and 28C are selected as a third test vector and coupled to the first sensing channel and any one of electrodes 28A, 28B and 28C along with electrode 26 are selected as a fourth test vector and coupled to the second sensing channel. Sensing vector data is then obtained simultaneously for the third and fourth sensing vectors. In some instances, each of electrodes 28A, 28B and 28C may be paired with sensing electrode 26 one at a time or in combinations of two or all three for testing additional sensing vectors. Furthermore, defibrillation electrode 24 may be selected with any of the sensing electrodes 26 and 28 for testing additional sensing vectors.

At block 206, the initially selected sensing vector(s) are used to acquire a respective cardiac electrical signal at block 206. The cardiac electrical signal may be an ECG signal when extra-cardiac electrodes are used to sense the signal. In other examples, the signal an EGM signal when endocardial, epicardial or coronary sinus sensing electrodes are used. The cardiac electrical signal may include signals attendant to the depolarization and repolarization of the myocardium, such as P-waves in the atria and R-waves and T-waves in the ventricles. When an ECG signal is being received, the P-waves and T-waves may have very low amplitudes compared to R-waves.

Vector selection parameters are determined from the sensed cardiac signal at block 208 for each of the selected sensing vectors. Determination of vector selection parameters may include analyzing the cardiac signal during an analysis window. In some cases, the analysis window may be an n-second cardiac signal segment, e.g., a 3 second, 8 second, 10 second or other duration signal segment. The n-second analysis window may be acquired and stored over the desired duration independent of the timing of cardiac events such as R-waves. Some examples of vector selection parameters that may be used in the techniques disclosed herein may be determined using signal sample points obtained over the n-second segment, such as a determination of signal frequency content, signal amplitude content, signal slope content or other overall cardiac electrical signal content that may indicate the proportion of the cardiac electrical signal that is true cardiac signal content vs. noise or other non-physiological signal content.

In other cases, a vector selection parameter may be determined from a cardiac signal analysis window that is set across one cardiac cycle or a portion thereof based on sensing a cardiac event. For example, an R-wave may be sensed and used to set a cardiac signal analysis window that extends from one R-wave to the next sensed R-wave or extends from a time earlier than a sensed R-wave to a time after the sensed R-wave to encompass the R-wave or a QRS complex. One or more cardiac signal analysis windows may be applied to a sensed cardiac signal depending upon the particular vector selection parameters being determined.

A vector selection parameter is generally a parameter that is an indication of the quality and reliability of the cardiac electrical signal for sensing true cardiac events (e.g., R-waves, P-waves, or T-waves), measuring cardiac event intervals, and/or analyzing cardiac event signal morphology or wave shape such as the shape of a QRS complex. Vector selection parameters may include one or more parameters relating to the signal strength of selected cardiac events such as R-waves, T-waves and/or P-waves that are desired to be sensed by a sensing channel of the IMD sensing module. Selection parameters relating to the strength of cardiac event signals may include, but are not limited to, R-wave amplitude, P-wave amplitude, T-wave amplitude, QRS signal width, or R-wave slope. A vector selection parameter determined as an amplitude or other cardiac event signal feature that is indicative of the strength of cardiac event signal may be determined as an average feature of multiple cardiac events. To illustrate, an R-wave amplitude may be determined as the mean peak amplitude of eight to ten (or other desired number) of consecutively sensed R-waves. Alternatively, R-wave amplitude may be determined as the nth lowest peak amplitude out of a predetermined number of R-waves, e.g., the lowest or $2^{nd}$ lowest peak amplitude out of 10 consecutive R-waves. It is recognized that numerous vector selection parameters may be determined that are an indicator of the strength of cardiac event signals that are desired to be sensed by the sensing module 86 or used by control module 80 for detecting and discriminating heart rhythms.

Vector selection parameters may additionally or alternatively include parameters indicative of the clarity of the cardiac event signal(s) of interest. An indication of cardiac event signal clarity may be a proportion of desired cardiac signal content vs. undesired signal content, which may include physiological and non-physiological noise. For example, a vector selection parameter that is an indication of the frequency or slope content of the cardiac signal over a signal analysis window may be determined. The low slope content (LSC) is one vector selection parameter that may be determined as an indicator of signal clarity. For example, when R-waves are being sensed from an ECG signal received by IMD 14, e.g., for determining ventricular rate or RR intervals, R-waves are the desired cardiac event signal. R-waves separated by a relatively flat baseline signal represent the desired cardiac signal content. P-waves, T-waves, and other physiologic or non-physiological noise may represent the undesired signal content. Non-physiological noise may include electromagnetic interference or other noise that is generally higher in frequency than desired cardiac event signal content and may be present in short bursts of time. Other noise may be caused by electrode motion due to patient body motion, muscle activity, or respiratory motion.

A cardiac signal having a relatively flat or clean baseline with high slope, narrow QRS complexes will have a high LSC, particularly during low or resting heart rates, indicating high signal clarity for sensing the desired R-waves. In contrast, bursts of high-frequency, non-physiological noise decrease the LSC of the cardiac signal during an-second time interval. Wide, large amplitude P-waves or T-waves that may be oversensed as R-waves will also decrease the LSC. Additionally, baseline noise or variation due to respiration, body motion or other non-desired cardiac signal content may decrease the LSC. As such, LSC may be one parameter determined during a sensing vector test for identifying acceptable sensing vectors. A sensing vector having high signal clarity as indicated by a high LSC is an acceptable sensing vector and is more desirable for use in determining a patient's heart rhythm than other vectors having lower signal clarity that may result in undersensing or oversensing of the desired cardiac event signal.

In one example, LSC is determined as the ratio of the number of slope data points less than a low slope threshold to the total number of data points during an n-second time period. Slope data points are determined as the sample-to-sample differences of the raw cardiac signal. In one example, the low slope threshold may be defined as a percentage, for example 10%, of the largest absolute slope determined from the n-second signal segment. The low slope content is then determined as the number of slope data points having an absolute value less than the low slope threshold to the total number of slope data points occurring in the n-second analysis time period.

One or more n-second time periods may be analyzed to obtain multiple LSC values for a given vector. An average, median, mode or other metric of the multiple LSC values may be determined as the indicator of signal clarity for the sensing vector.

Other vector selection parameters may include a ratio of R-wave amplitude to an averaged baseline amplitude, P-wave amplitude to an averaged baseline amplitude, T-wave amplitude to an averaged baseline amplitude, R-wave amplitude to T-wave amplitude, or other ratio of cardiac events that are to be sensed by the sensing module 86 to non-cardiac events or cardiac events that are not desired to be sensed by the sensing module. For example, T-waves are cardiac events that may be oversensed as R-waves and are therefore events that are not desired to be sensed by the sensing module 86 in some applications. Methods used to determining vector selection parameters may correspond to techniques generally disclosed in U.S. Pat. No. 7,904,153 (Greenhut, et al.), incorporated herein by reference in its entirety.

The vector selection parameters may be determined at block 208 by IMD control module 80 and stored in memory 82 for each of the selected sensing vectors. In some examples, a sample signal segment of the cardiac electrical signal from which selection parameters were determined may also be stored. After determining vector selection parameters for the currently selected sensing vectors, the IMD control module 80 determines whether additional sensing vectors are available at decision block 210. The process returns to block 204 to select the next vector(s) to be tested until selection parameters have been stored for all available sensing vectors.

The sensing vectors tested by the IMD 14 may be a fixed set of available sensing vectors that is not programmable by a user. Alternatively, a user may be able to designate which vectors should be evaluated prior to starting the test.

Upon verifying that the sensing vector test is complete at block 210, the IMD control module 80 provides the telemetry module 88 with the sensing vector data, which is transmitted to the external device 40 at block 212. In one example, the user initiates the sensing vector test using the external device 40. The IMD 14 automatically steps through the selection of each available test sensing vector, determines vector selection parameters for each vector and transmits the sensing vector data to the external device 40 in response to receiving the "start test" command from the external device 40. In other examples, the sensing vector test may be performed automatically by the IMD and the sensing vector data is transmitted at block 212 during the next telemetry session with external device 40. The transmitted data includes the vector selection parameters determined for each sensing vector tested and may include a sample cardiac signal segment for each sensing vector tested. The transmitted data may further include vector acceptability criteria if the vector acceptability criteria have been programmed to unique settings in IMD 14 for the given patient.

In other examples, the sensing vector data transmitted from IMD 14 to external device 40 during a sensing vector test includes raw cardiac electrical signal and corresponding sensing vector used to acquire the signal. The raw cardiac electrical signal may be transmitted to the external device 40, in real time or after acquiring and storing an n-second signal segment for each test vector. The external device processor 52 may determine the vector selection parameters from the transmitted cardiac electrical signal.

At block 214, the external device 40 produces a vector selection display. The external device processor 52 provides sensing vector data to user display 54. For example, the vector selection parameter values for each sensing vector are provided to the user display 54. In some examples, external processor 52 may compute a vector selection index at block 214 using the sensing vector data received from IMD 14 and provide the vector selection index or an indication of recommended sensing vectors to user display 54. Determination of a vector selection index used to identify recommended sensing vectors is described in greater detail below.

The external device processor 52 further provides the vector acceptability criteria that is stored in external device memory 53 or received from IMD 14 to user display 54 at block 214. In response to the received sensing vector data and vector acceptability criteria, user display 54 produces a display as part of a graphic user interface that includes a graphic display of the vector selection parameter data relative to the vector acceptability criteria. The display may further include a tabular listing of the vector selection parameter data.

Figure 6:
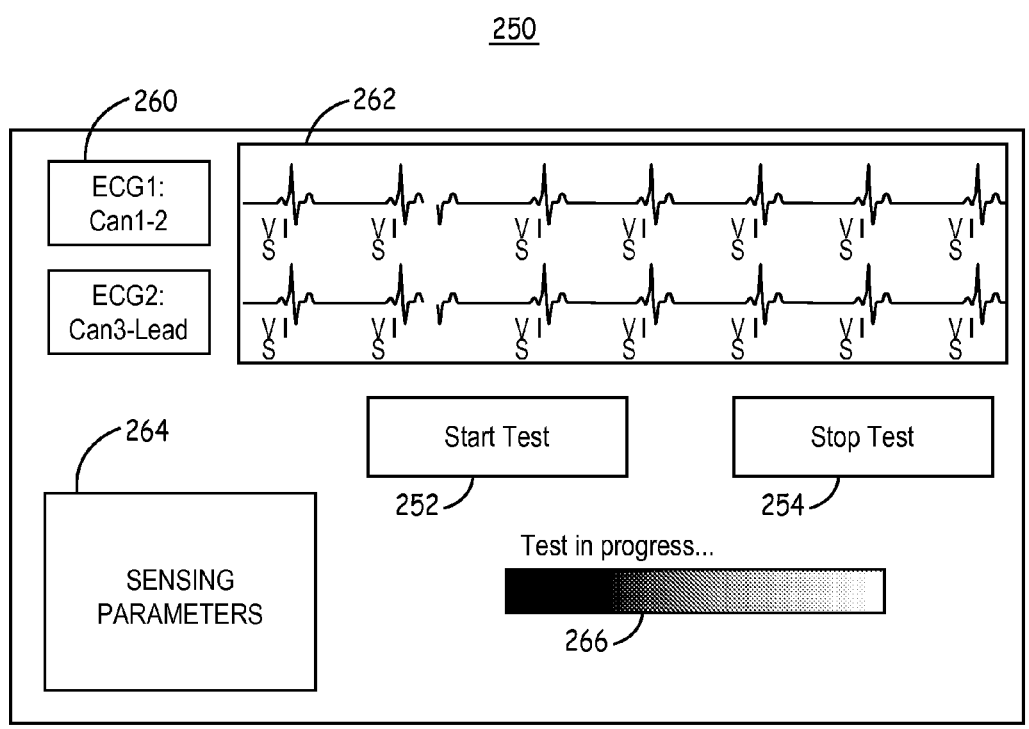
FIG. 6 is a diagram of a graphical user interface (GUI) produced by the IMD system user display for enabling a user to manually start the sensing vector test.

FIG. 6 is a diagram of a graphical user interface (GUI) 250 produced by the user display 54 for enabling a user to manually start the sensing vector test. GUI 250 includes a start test button 252 and may include a stop test button 254. When the start test button 252 is selected by a user, a test in progress bar 266 may indicate the test is under way and may indicate a time or percentage toward completion. The patient may be advised to stay still or assume a desired position during the test. The stop test button 254 may be used if movement or noise is introduced while the test is underway. Once the sensing vector test has been completed, the GUI 250 may automatically be replaced by a test result GUI, such as GUI 300 as shown in FIG. 7.

The start test GUI 250 may include other features such as an indicator of currently programmed sensing vectors 260 with a real-time display of corresponding ECG signals 262 indicating sensed events, e.g., ventricular sensed events (VS). Sensing control parameters 264 may also be displayed for each sensing vector, such as sensitivities, blanking intervals, sensing thresholds, etc., which are programmed for the currently programmed sensing vectors and/or used by the IMD 14 during the sensing vector test.

Figure 7:
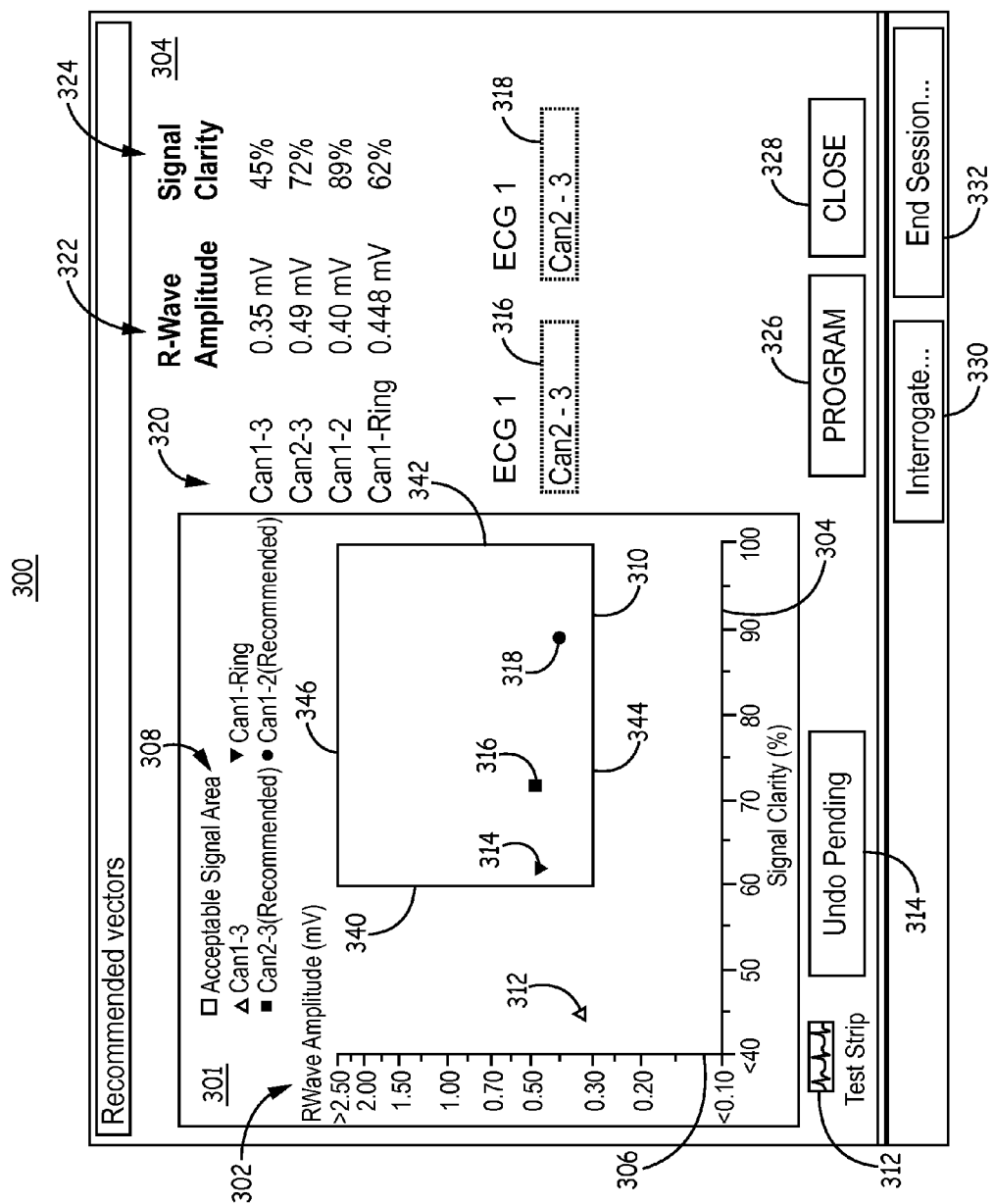
FIG. 7 is a diagram of a graphical user interface produced by the IMD system user display for presenting sensing vector data.

FIG. 7 is a diagram of a GUI 300 produced by the user display 54 for presenting vector selection data upon completion of a sensing vector test. The GUI 300 includes a graphical display area 301 and a tabular display area 304. The graphical display area 301 includes a two-dimensional plot 302 and a corresponding legend 308. The plot 302 has an x-axis 304 corresponding to a first vector selection parameter and a y-axis 306 corresponding to a second vector selection parameter. In this example plot 302 is a two-dimensional plot produced to represent two different vector selection parameters. It is contemplated that plot 302 could be a one dimensional plot or a three-dimensional plot produced to represent a single selection parameter or three selection parameters, respectively. In other examples, it is contemplated that four or more vector selection parameters may be presented in other charts or graphical formats, such as a bar graph, however a one-, two- or three-dimensional plot of one, two or three vector selection parameters for each sensing vector may be the easiest to understand by a user.

In the example shown, R-wave amplitude is shown along the y-axis 306 as a vector selection parameter relating to cardiac event signal strength and signal clarity is shown along the x-axis 304 as a vector selection parameter relating to the proportion of cardiac signal content of the sensing vector signal. The R-wave amplitude may be determined in mV or may be normalized, e.g., by the highest R-wave amplitude measured for any of the sensing vectors. Signal clarity is determined in this example as the LSC as described above. Signal clarity is expressed as a percentage and can range from 0% (no slope points falling below a low slope threshold) to 100% (all slope points falling below the low slope threshold).

Each sensing vector included in the sensing vector test is represented in the plot 302 by a symbol as indicated by legend 308. Each sensing vector is represented by its respective vector selection parameters determined for that vector. In this example, four ECG sensing vectors have been tested using the housing based electrodes 28A (Can1), 28B (Can2) and 28C (Can3) and the lead-based electrode 26 (Ring). The selection parameters for vector Can1-3 (between electrodes 28A and 28C as shown in FIG. 2) are plotted using a triangular symbol 312 at the x-y coordinates corresponding to the R-wave amplitude and signal clarity determined from the ECG signal acquired from vector Can1-3. Similarly, the other three tested vectors Can 2-3 Can 1-Ring, and Can 1-2 are each represented by respective symbols 314, 316 and 318 as designated in legend 308 and plotted in plot 302 at the x-y coordinates defined by the R-wave amplitude and signal clarity parameter values determined for each respective vector.

To aid the user in understanding which sensing vectors are acceptable and which are not, a vector acceptability region 310 is displayed that represents the vector acceptability criteria. In this example, the region 310 is a rectangle having a left, lower x-boundary 340 corresponding to the signal clarity vector acceptability threshold of 60%. Region 310 has a right, upper x-boundary 342 corresponding to the maximum possible value of the signal clarity parameter of 100%. The bottom, lower y-boundary 344 is defined by the R-wave amplitude vector acceptability threshold of 0.3 mV and the top, upper y-boundary 346 may be set to a maximum sensing range of the sensing module 86. It is understood that the particular boundaries of region 310 represent illustrative vector acceptability criteria and the particular thresholds or ranges used to define vector acceptability criteria may vary between embodiments. The acceptability region 310 is set based on the particular acceptability criteria defined for the particular application and/or patient.

The vector acceptability region 310 denotes all values of both of the vector selection parameters (R-wave amplitude and signal clarity) that together satisfy the vector acceptability criteria. In the illustrative example shown, points 314, 316 and 318 representing vectors Can1-Ring, vector Can 2-3, and vector Can1-2 all fall within the vector acceptability region 310. Of these, the right-most points 316 and 318 have higher signal clarity with all three having similar R-wave amplitude. As such, vectors Can2-3 and Can1-2 which correspond to points 316 and 318, respectively, are automatically designated as recommended vectors in the legend 308.

When multiple vectors meet the vector acceptability criteria based on thresholds, ranges or other requirements applied to individual vector selection parameters, vector selection criteria may be applied to the vectors meeting the acceptability criteria. In one embodiment, a selection index may be computed as a weighted combination of the vector selection parameters for all vectors meeting the vector acceptability criteria. For example, one of the R-wave amplitude or other parameter indicative of cardiac event signal strength or the signal clarity or other parameter indicative of the proportion of the cardiac signal content of the overall signal may be given a greater weight than the other parameter.

In one example, the external device processor 52 may compute a selection index (SI) for each of the vectors falling within the acceptability region 310 as SI=(LSC*W1+R-wave amplitude*W2)/((W1+W2)*R-wave amplitude*LSC)). If two sensing channels are available in sensing module 86, the two vectors resulting in the highest SI are designated as the recommended sensing vectors for monitoring the patient's heart rhythm. When processor 52 determines a recommended sensing vector based on selection criteria applied to acceptable vectors, e.g., by determining a selection index or other combination of vector selection parameters, processor 52 provides this data to user display 54 for generating the graphical user interface 300.

The recommended vectors selected by applying vector selection criteria to all vectors meeting the acceptability criteria may be automatically set and displayed as the pending sensing vector selections 316 and 318 in the tabular display area 304 for programming by the user. The pending values may be highlighted by a color, flashing display or other feature until the pending values have been programmed using program button 326.

The user may select the PROGRAM button 326 on GUI 300 to program the recommended vectors. The user may alternatively manually select different sensing vectors 316 and 318 from a drop down window.

The user may select a test strip display 312 to view a stored signal sample for each of the tested sensing vectors. The user may select the Undo Pending button 314 to clear the pending sensing vector selections 316 and 318 and may select different vectors or restart the sensing vector test.

In the tabular display area 304, each of the tested sensing vectors 320 may be listed along with their respective vector selection parameters, e.g., R-wave amplitude values 322 and signal clarity values 324. In this way, the user has both a tabular and graphical display of the sensing vector data to facilitate his/her understanding of which vectors are acceptable and which are not and why the automatically recommended sensing vectors were selected as the pending sensing vectors 316 and 318 out of the vectors meeting the acceptability criteria.

GUI 300 may include other features such as a surface ECG display (not illustrated), a Close button 328 to leave the sensing vector selection GUI 300 to move to another programming or data display screen, an Interrogate button 330 for sending an interrogation command to the IMD 14, and an end session button 332 for ending the telemetry session with the IMD 14 after all desired programming has taken place.

Thus, a method and apparatus for acquiring and displaying sensing vector data have been presented in the foregoing description with reference to specific embodiments. It is appreciated that various modifications to the referenced embodiments may be made without departing from the scope of the disclosure as set forth in the following claims.

The invention claimed is:

1. A method, comprising:
sensing cardiac electrical signals across a plurality of sensing vectors selected from a plurality of implantable electrodes coupled to an implantable medical device;
determining at least one sensing vector selection parameter from the sensed cardiac electrical signals for each of the plurality of sensing vectors;
wirelessly transmitting the determined sensing vector selection parameters by an implantable telemetry module;
receiving the transmitted sensing vector selection parameters by an external telemetry module of an external medical device;
providing, by an external processor coupled to the external telemetry module, sensing vector acceptability criteria and at least a portion of the sensing vector selection parameters to a user display, the sensing vector acceptability criteria comprising at least one vector acceptability threshold; and
displaying the sensing vector acceptability criteria and at least the portion of the sensing vector selection parameters as part of a graphical user interface for programming a sensing vector used by the implantable medical device for monitoring a patient's heart rhythm, wherein displaying the vector acceptability criteria comprises displaying the at least one vector acceptability threshold relative to at least the portion of the sensing vector selection parameters determined for each of the plurality of sensing vectors.

2. The method of claim 1, wherein providing the vector acceptability criteria further comprises providing a vector acceptability region of the vector selection parameter, the vector acceptability region defined at least in part by the vector acceptability threshold and an upper boundary, the method further comprising displaying the sensing vector acceptability criteria as the vector acceptability region on a plot of at least the portion of the sensing vector data, the vector acceptability region representing the vector acceptability criteria.

3. The method of claim 1, wherein displaying at least the portion of the sensing vector selection parameters comprises generating a plot of the vector selection parameters and displaying the sensing vector acceptability criteria as a region of the plot.

4. The method of claim 1, wherein determining the at least one sensing vector selection parameter comprises determining a parameter indicative of cardiac event signal strength for each of the plurality of sensing electrode vectors.

5. The method of claim 4, wherein determining the sensing vector selection parameter indicative of cardiac event signal strength comprises determining an R-wave amplitude.

6. The method of claim 1, wherein determining the at least one sensing vector selection parameter comprises determining a parameter indicative of a proportion of physiological signal content of the cardiac electrical signal for each of the plurality of sensing electrode vectors.

7. The method of claim 6, wherein determining the parameter indicative of the proportion of physiological signal content comprises determining, across a signal analysis window, a percentage of signal sample points that correspond to a slope that is less than a slope threshold.

8. The method of claim 1, further comprising automatically identifying at least one recommended sensing vector of the plurality of sensing vectors in response to the at least one sensing vector selection parameter and displaying the at least one recommended sensing vector as a pending sensing vector to be programmed in the implantable medical device by the external medical device.

9. The method of claim 1, further comprising:

determining a plurality of vector selection parameters from the sensing vector data for each of the plurality of sensing vectors;

determining a selection index from the vector selection parameters for each of the plurality of sensing vectors meeting the displayed vector acceptability criteria; and selecting at least one recommended sensing vector of the plurality of sensing vectors in response to the determined selection indices;

displaying as part of the graphical user interface the at least one recommended sensing vector as a pending sensing vector to be programmed in the implantable medical device.

10. The method of claim 1, further comprising:

determining an R-wave amplitude from the sensing vector data for each of the plurality of sensing vectors;

determining a low slope content of the cardiac electrical signal by determining, across a cardiac signal analysis window, a proportion of cardiac electrical signal sample points corresponding to a slope that is less than a slope threshold for each of the plurality of sensing vectors, wherein displaying at least a portion of the sensing vector data comprises displaying a point for each of the plurality of sensing vectors in a two-dimensional plot, each point for each respective one of the plurality of sensing vectors being defined by x-y coordinates corresponding to the R-wave amplitude and the determined low slope content determined for each respective one of the plurality of sensing vectors; and displaying the vector acceptability criteria as a vector acceptability region of the two-dimensional plot, the vector acceptability region defined by an R-wave amplitude selection threshold and a low slope content selection threshold.

11. A system, comprising:

a plurality of implantable electrodes;

an implantable medical device comprising:

a sensing module configured to sense cardiac electrical signals across a plurality of sensing vectors selected from the plurality of electrodes, a control module coupled to the sensing module and configured to determine at least one sensing vector selection parameter for each of the plurality of sensing vectors from the sensed cardiac electrical signals, and a telemetry module configured to transmit the sensing vector selection parameters;

a user display;

an external telemetry module configured to receive the transmitted sensing vector selection parameters;

an external processor coupled to the user display and the external telemetry module, the external processor configured to provide sensing vector acceptability criteria and at least a portion of the sensing vector selection parameters to the user display, the sensing vector acceptability criteria comprising at least one vector acceptability threshold;

the user display configured to display the sensing vector acceptability criteria and the sensing vector selection parameters received from the external processor as part of a graphical user interface for programming a sensing vector used by the implantable medical device for monitoring a patient's heart rhythm, the user display configured to display the sensing vector acceptability criteria by displaying the at least one vector acceptability threshold relative to at least the portion of the sensing vector selection parameters determined for each of the plurality of sensing vectors.

12. The system of claim 11, wherein;

the external processor is configured to provide the sensing vector acceptability criteria by providing a vector acceptability region of the vector selection parameter, the vector acceptability region defined at least in part by the vector acceptability threshold and an upper boundary, the user display is configured to display the sensing vector acceptability criteria by displaying the vector acceptability region on a plot of at least the portion of the sensing vector data, the vector acceptability region representing the vector acceptability criteria.

13. The system of claim 11, wherein the user display is configured to display at least the portion of the sensing vector selection parameters by generating a plot of the vector selection parameters and to display the sensing vector acceptability criteria as a region of the plot.

14. The system of claim 11, wherein determining the at least one sensing vector selection parameter comprises determining a parameter indicative of cardiac event signal strength for each of the plurality of sensing electrode vectors.

15. The system of claim 14, wherein determining the sensing vector selection parameter indicative of cardiac event signal strength comprises determining an R-wave amplitude.

16. The system of claim 11, wherein determining the at least one sensing vector selection parameter comprises determining a parameter indicative of a proportion of physiological signal content of the cardiac electrical signal for each of the plurality of sensing electrode vectors.

17. The system of claim 16, wherein determining the parameter indicative of the proportion of physiological signal content comprises determining, across a signal analysis window, a percentage of signal sample points that correspond to a slope that is less than a slope threshold.

18. The system of claim 11, wherein the external processor is further configured to identify at least one recommended sensing vector of the plurality of sensing vectors in response to the at least one sensing vector selection parameter and provide the recommended sensing vector to the user display, the user display configured to display the recommended sensing vector as a pending sensing vector to be programmed in the implantable medical device.

19. The system of claim 11, wherein at least one of the control module of the implantable medical device and the external processor is configured to:
    determine a plurality of vector selection parameters from the sensing vector data for each of the plurality of sensing vectors;
    determine a selection index from the plurality of vector selection parameters for each of the plurality of sensing vectors meeting the vector acceptability criteria; and
    select at least one recommended sensing vector of the plurality of sensing vectors in response to the determined selection indices;
    provide the at least one recommended sensing vector to the user display;
    wherein the user display is configured to display as part of the graphical user interface the at least one recommended sensing vector as a pending sensing vector to be programmed in the implantable medical device.

20. The system of claim 11, wherein at least one of the control module of the implantable medical device and the external processor is configured to:
    determine an R-wave amplitude from the cardiac electrical signals for each of the plurality of sensing vectors, and
    determine a low slope content of the cardiac electrical signal for each of the plurality of sensing vectors by determining, across a cardiac signal analysis window, a proportion of cardiac electrical signal sample points corresponding to a slope that is less than a slope threshold,
wherein the user display is configured to:
    display a point for each of the plurality of sensing vectors in a two-dimensional plot, each point for each respective one of the plurality of sensing vectors being defined by x-y coordinates corresponding to the R-wave amplitude and the low slope content determined for each respective one of the plurality of sensing vectors, and
    display the vector acceptability criteria as a vector acceptability region of the two-dimensional plot, the vector acceptability region defined by an R-wave amplitude selection threshold and a low slope content selection threshold.

21. The system of claim 11, wherein:
the user display is configured to:
    display the sensing vector data by at least plotting the sensing vector acceptability parameter for each of the plurality of sensing vectors along an axis, and
    display the sensing vector acceptability criteria by plotting a boundary of a vector acceptability region along the axis, the boundary defined by the vector acceptability threshold.

22. The system of claim 11, wherein the user display is configured to display the sensing vector acceptability criteria and the sensing vector data in a plot by:
    displaying a point for each of the plurality of sensing vectors in the plot, each point for each respective one of the plurality of sensing vectors being defined by plot coordinates corresponding to the at least one sensing vector selection parameter determined for each respective one of the plurality of sensing vectors, and
    displaying a boundary corresponding to the at least one vector acceptability threshold value in the plot relative to the displayed points.

23. A non-transitory, computer-readable medium storing a set of instructions, which when executed by a processor of a medical device system causes the system to:
    sense cardiac electrical signals across a plurality of sensing vectors selected from a plurality of implantable electrodes coupled to an implantable medical device;
    determine at least one sensing vector selection parameter from the sensed cardiac electrical signals for each of the plurality of sensing vectors;
    wirelessly transmit the determined sensing vector selection parameters by an implantable telemetry module;
    receive the transmitted sensing vector selection parameters by an external telemetry module of an external medical device;
    provide, by an external processor coupled to the external telemetry module, sensing vector acceptability criteria and at least a portion of the sensing vector selection parameters to a user display, the sensing vector acceptability criteria comprising at least one vector acceptability threshold; and
    display the sensing vector acceptability criteria and at least the portion of the sensing vector selection parameters as part of a graphical user interface for programming a sensing vector used by the implantable medical device for monitoring a patient's heart rhythm,
    wherein displaying the sensing vector acceptability criteria comprises displaying the at least one vector acceptability threshold relative to at least the portion of the sensing vector selection parameters determined for each of the plurality of sensing vectors.

* * * * *